(12) United States Patent
Ren (10) Patent No.: US 10,751,047 B2
(45) Date of Patent: Aug. 25, 2020

(54) HANGABLE DISPOSABLE BAG FOR SUTURES AND OTHER MEDICAL WASTE

(71) Applicant: Medline Industries, Inc, Mundelein, IL (US)

(72) Inventor: XingQuan Ren, Skokie, IL (US)

(73) Assignee: Medline Industries, Inc., Northfield, IL (US)

( * ) Notice: Subject to any disclaimer, the term of this patent is extended or adjusted under 35 U.S.C. 154(b) by 1148 days.

(21) Appl. No.: 14/335,670

(22) Filed: Jul. 18, 2014

(65) Prior Publication Data

US 2016/0015388 A1     Jan. 21, 2016

(51) Int. Cl.

| | | |
|---|---|---|
| *A61B 17/06* | (2006.01) | |
| *B65F 1/00* | (2006.01) | |
| *B29C 65/50* | (2006.01) | |
| *A61B 50/36* | (2016.01) | |
| *B29L 31/00* | (2006.01) | |
| *A61B 50/30* | (2016.01) | |
| *A61B 50/00* | (2016.01) | |

(52) U.S. Cl.
CPC ........ *A61B 17/06161* (2013.01); *A61B 50/36* (2016.02); *B65F 1/002* (2013.01); *B65F 1/0013* (2013.01); *A61B 2050/002* (2016.02); *A61B 2050/314* (2016.02); *B29L 2031/7129* (2013.01); *B65F 2210/1125* (2013.01)

(58) Field of Classification Search
CPC .......... A61B 17/06161; A61B 19/0288; A61B 19/029; B29C 65/50; B65F 1/002; B65F 1/0006; B65D 33/30; B65D 33/02; B65D 31/00

USPC ............................................ 383/33, 119, 120
See application file for complete search history.

(56) References Cited

U.S. PATENT DOCUMENTS

| | | | |
|---|---|---|---|
| 2,776,615 A | 1/1957 | Frey | |
| 3,290,854 A | 12/1966 | MacMurray | |
| 3,426,958 A * | 2/1969 | Gore ...................... | B65D 33/14 206/806 |
| 3,589,595 A * | 6/1971 | White .................... | B65D 33/14 206/806 |
| D278,974 S | 5/1985 | Ray | |

(Continued)

FOREIGN PATENT DOCUMENTS

GB          2364375 A   *   1/2002  ......... B23Q 11/0053

OTHER PUBLICATIONS

"Xodus Medical Solutions", *Xodus Medical Solutions: Product Catalog: Suture Bags*; Publication date unknown but believed to be prior to filed of present application; www.xodusmedical.com/Products/21/Suture-Bags.

(Continued)

*Primary Examiner* — Christopher R Demeree
(74) *Attorney, Agent, or Firm* — Philip H. Burrus, IV (57) ABSTRACT

A bag (200) includes an elongated bag body (201). The elongated bag body can define two opposing ends, namely an openable end (202) and a closed end (203). An adhesive strip (308) can be disposed upon an exterior of the elongated bag body. The adhesive strip can be disposed in a horizontal orientation parallel to the openable end. A flexible strip (208) can be disposed upon the exterior of the elongated bag body. The flexible strip can be bendable to retain the openable end in an open position (601). The bag is suitable for use as a suture collection bag.

20 Claims, 12 Drawing Sheets

(56) References Cited

U.S. PATENT DOCUMENTS

| | | | |
|---|---|---|---|
| 4,761,079 A * | 8/1988 | Wolske | B65D 33/30 |
| | | | 383/62 |
| 5,005,264 A * | 4/1991 | Breen | B65D 33/1691 |
| | | | 24/30.5 R |
| 5,203,458 A * | 4/1993 | Cornwell | A61B 19/029 |
| | | | 206/278 |
| 5,624,419 A | 4/1997 | Ersek et al. | |
| D396,002 S | 7/1998 | Bell | |
| 5,814,382 A | 9/1998 | Yannuzzi, Jr. | |
| 5,915,839 A * | 6/1999 | Dennis | B65F 1/0006 |
| | | | 383/11 |
| 6,033,392 A | 3/2000 | Frey et al. | |
| 6,685,058 B2 * | 2/2004 | Redmond | A45D 34/04 |
| | | | 222/107 |
| 6,899,460 B2 * | 5/2005 | Turvey | B65D 33/007 |
| | | | 383/33 |
| D507,179 S | 7/2005 | King et al. | |
| D597,832 S | 8/2009 | Bischoff et al. | |
| D653,534 S | 2/2012 | Shinn | |
| 8,371,448 B1 * | 2/2013 | Reaux | A61B 19/029 |
| | | | 206/362 |
| D690,197 S | 9/2013 | Kessler, Jr. et al. | |
| D718,628 S | 12/2014 | Lee | |
| 2003/0232708 A1 | 12/2003 | Rabiea | |
| 2007/0088299 A1 | 4/2007 | Ayre | |
| 2008/0285893 A1 | 11/2008 | Zehir | |
| 2011/0052100 A1 | 3/2011 | Eisenberg et al. | |
| 2013/0308880 A1 | 11/2013 | Jenkins | |
| 2014/0161372 A1 | 6/2014 | Sulpizio et al. | |
| 2016/0015388 A1 | 1/2016 | Ren | |

OTHER PUBLICATIONS

Johnston, Nathan M., "NonFinal OA", U.S. Appl. No. 29/496,976, filed Jul. 18, 2014; dated Aug. 8, 2016.

* cited by examiner

HANGABLE DISPOSABLE BAG FOR SUTURES AND OTHER MEDICAL WASTE

BACKGROUND

1. Technical Field

This disclosure relates generally to bags, and more particularly to bags for disposal of medical waste.

2. Background Art

Medical procedures produce waste. Waste products can include soft materials, such as gauze, bandages, or towels. Waste products can also include items with sharp points or edges, including scissors, needles, scalpels, blades, shavers, catheter needles, trocars, and other puncturing or cutting items, which are referred to as "sharps" due to their cutting or puncturing components. Sharps are generally disposed of in a rigid container known as a "sharps container." Soft waste products can be collected in non-rigid containers. One or the more popular containers for collecting soft waste is a simple paper bag, which can leak and tear. It would be advantageous to have an improved container for disposing soft waste generated during medical procedures.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Figure 1:
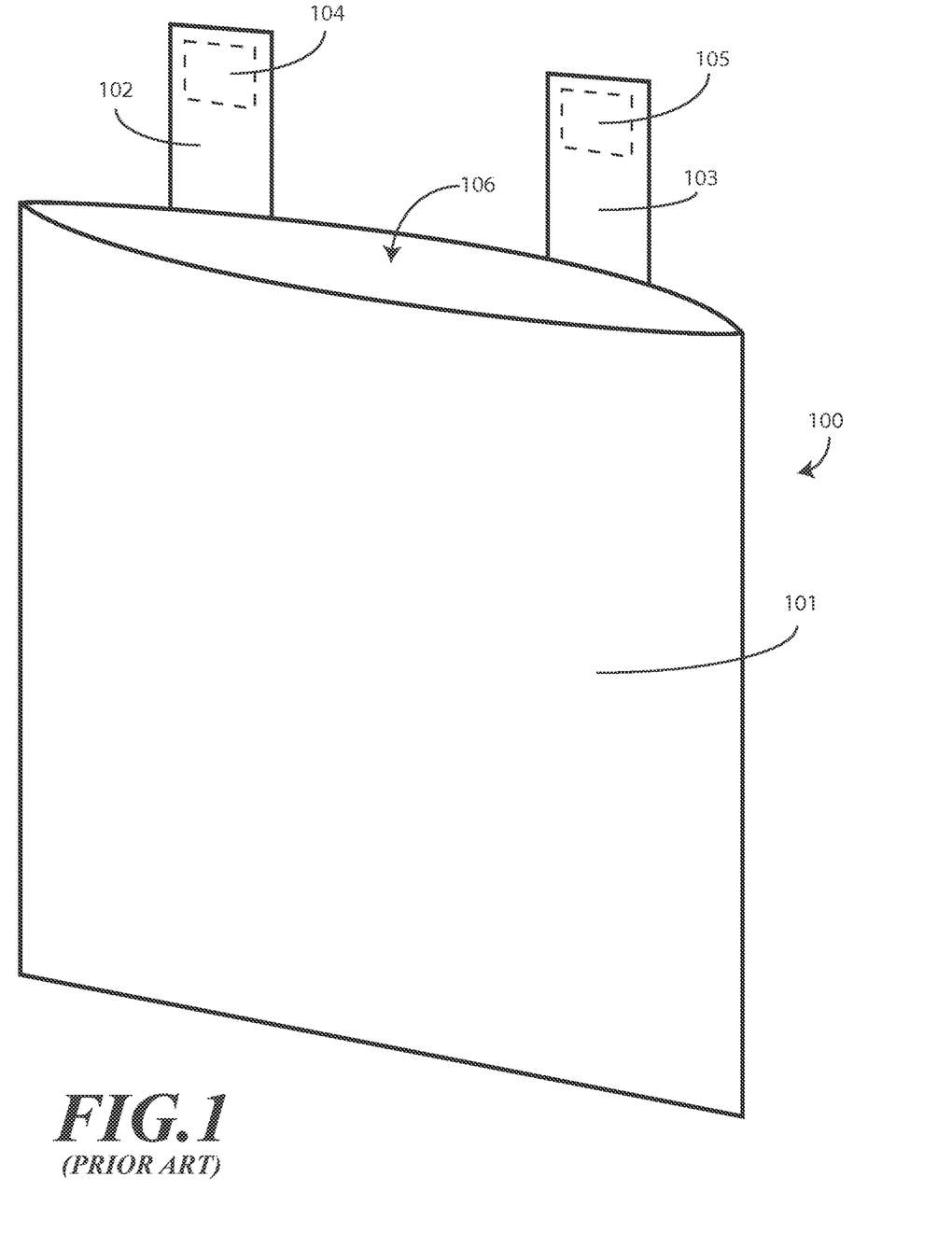
FIG. 1 illustrates a prior art soft medical waste disposal bag.

Waste disposal bags are commonly used in medical environments to collect soft waste products. For example, a waste disposal bag may be used in a hospital operating room to collect soft waste including sutures, bandages, gauze, paper products, and so forth. A prior art waste disposal bag 100 is shown in FIG. 1. The prior art waste disposal bag 100 is manufactured from paper. A first problem with the prior art waste disposal bag 100 is that paper is not liquid impervious. Accordingly, if gauze or bandages have absorbed liquids or blood, these liquids can penetrate into, or through the body 101 of the prior art waste disposal bag 100. This can cause the body 101 of the prior art waste disposal bag 100 to weaken or rupture.

The prior art waste disposal bag 100 is provided with two vertical tabs 102,103. Each of the vertical tabs 102,103 is made from paper. Each of the vertical tabs 102,103 has an adhesive square 104,105 attached thereto. The adhesive squares 104,105 typically measure only about 0.75 cm×1.5 cm. Users can attach the adhesive squares 104,105 to a surface to hang the prior art waste disposal bag 100 during use.

The vertical tabs 102,103 present a second problem with the prior art waste disposal bag 100. First, since the vertical tabs 102,103 are manufactured from paper, they are easily torn when objects are placed within the prior art waste disposal bag 100. Second, the adhesive squares 104,105 are small and are not capable of remaining attached to an object when weight is placed in the prior art waste disposal bag 100. When a failure of any of the body 101, the vertical tabs 102,103, or the adhesive squares 104,105 occurs in a medical environment, medical procedures such as surgeries may be disrupted. Further, such failures can result in unnecessary cleaning and sterilization requirements, as well as the spread of pathogens and disease. These weaknesses of the vertical tabs 102,103 are common complaints of users of the prior art waste disposal bag 100. As these complaints have been forthcoming for a long, long time, there is a long felt need to solve the issues associated with the prior art waste disposal bag 100.

Embodiments of the present disclosure provide a new and improved bag suitable for being used for the disposal of soft objects in medical environments. Embodiments of the disclosure provide improvements over the prior art waste disposal bag 100 by providing a bag having an elongated bag body that, in one embodiment, is manufactured from a thermoplastic material rather than paper. For example, in one embodiment the elongated bag body is manufactured from high-density polyethylene. Other similar materials can be used instead. The use of a material such as high-density polyethylene is advantageous in that it is stronger than paper, is liquid impervious, and is able to support a greater amount of weight.

In one embodiment, rather than using two vertical tabs 102,103 as does the prior art waste disposal bag 100, the bag employs a large, horizontally mounted adhesive strip disposed along an exterior of the elongated bag body. In one embodiment, this horizontally mounted adhesive strip is at least four centimeters long and at least one centimeter wide. This horizontally mounted adhesive strip can offer more than twice the adhesive surface of the adhesive squares 104,105 found in the prior art waste disposal bag 100, thereby allowing embodiments of the disclosure to support more weight without detaching from a surface.

In one embodiment, advantageously, the bag further includes a flexible strip disposed on an exterior of the elongated bag body. Embodiments of the disclosure contemplate that the opening 106 of the prior art waste disposal bag 100 is prone to closing and is difficult to maintain in an open position. Accordingly, a user may drop sutures or other medical waste on the floor due to the opening 106 closing. Embodiments of the disclosure solve this problem by providing a flexible strip that is bendable to retain an openable end of an elongated bag body in an open position.

Figure 2:
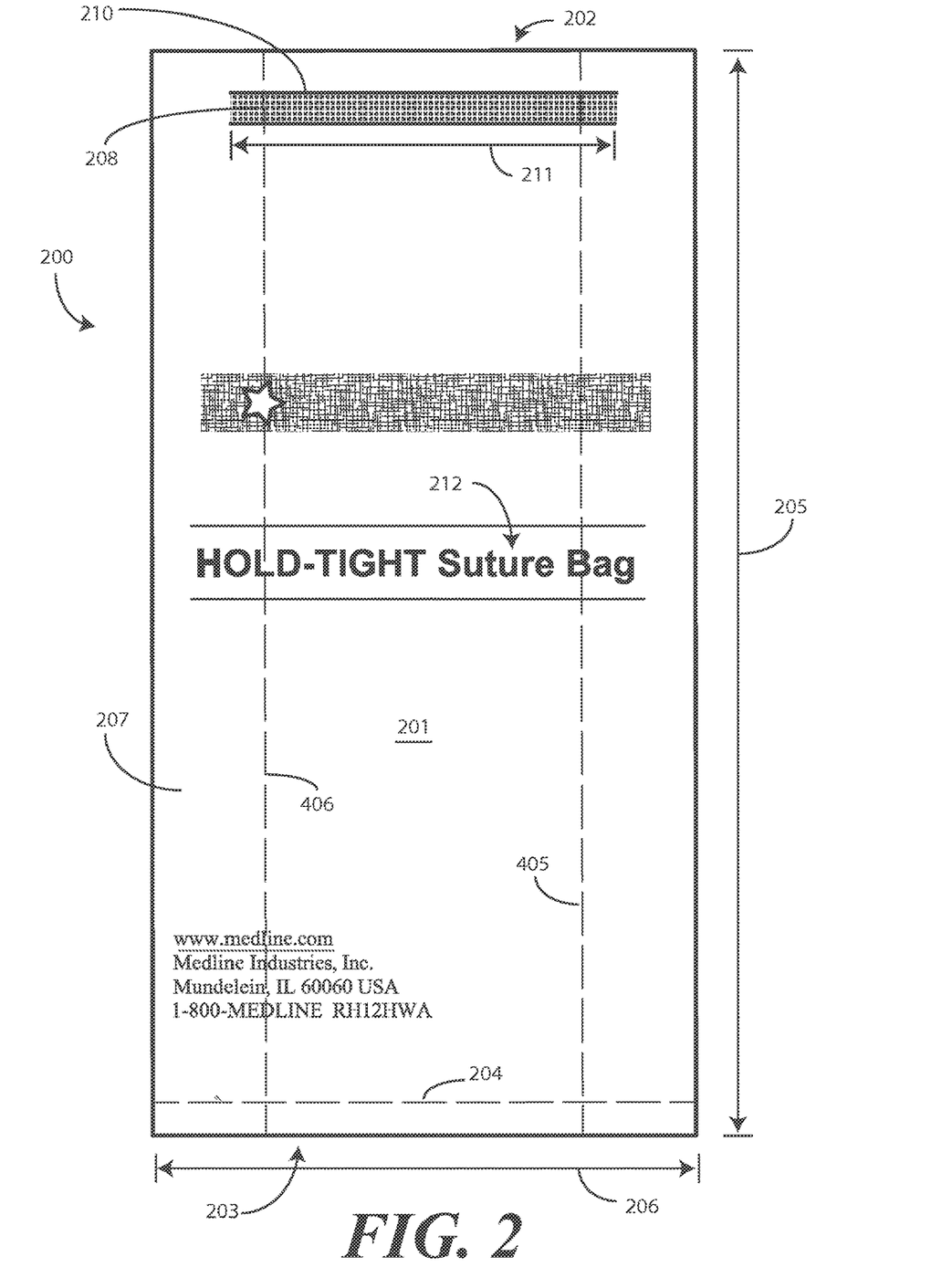
FIG. 2 illustrates a front elevation view of an explanatory bag in accordance with one or more embodiments of the disclosure.
Figure 3:
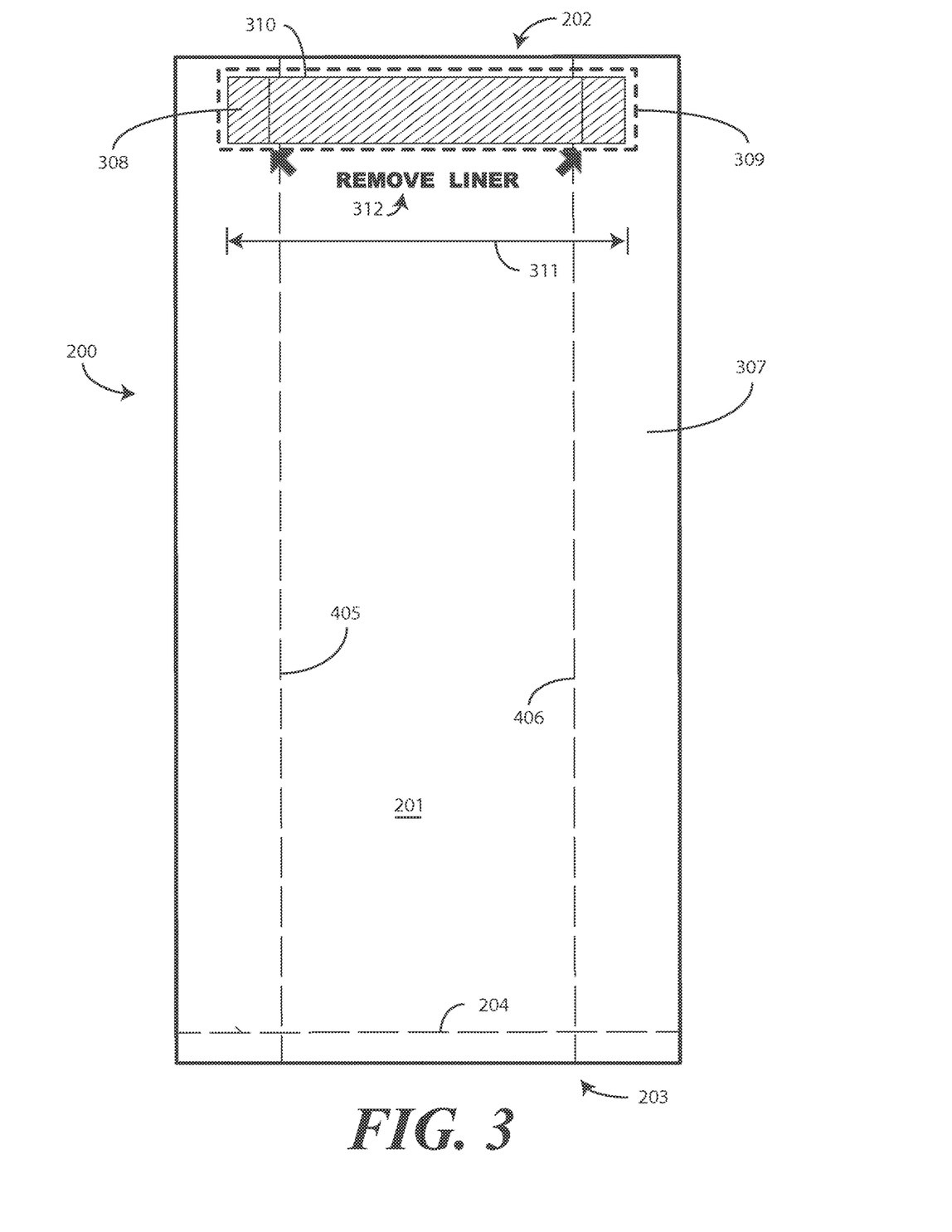
FIG. 3 illustrates a rear elevation view of an explanatory bag in accordance with one or more embodiments of the disclosure.

Turning now to FIGS. 2-5, illustrated therein is an explanatory bag 200 configured in accordance with one or more embodiments of the disclosure. In one embodiment, the bag includes an elongated bag body 201 defining two opposing ends, namely an openable end 202 and a closed end 203. In FIGS. 2 and 3, the bag 200 is shown in a flattened shape, with the openable end 202 in a closed position. By contrast, in FIGS. 4 and 5, the openable end 202 is shown in the open position.

In one embodiment, the closed end 203 is formed by creating a thermal seal 204 along one of the two opposing ends. In another embodiment, an adhesive seal or other seal can be substituted for the thermal seal 204 to form the closed end 203. Other methods of forming the closed end 203 will be obvious to those of ordinary skill in the art having the benefit of this disclosure. For example, in another embodiment the closed end 203 is formed by a thermal cutting operation during extrusion of the elongated bag body 201 to form a seal.

In one embodiment, the elongated bag body 201 is manufactured from a flexible material that allows the elongated bag body 201 to be folded or rolled for efficient storage or delivery. In one embodiment, the elongated bag body 201 is manufactured from a flexible thermoplastic such as high-density polyethylene. In one embodiment, the high-density polyethylene has a thickness of about 0.0016 inches, with a tolerance of plus or minus 0.00016 inches. Other materials and/or dimensions may also be used for the elongated bag body 201. For example, the elongated bag body 201 could be manufactured from low-density polyethylene in other embodiments. Other materials include other plastics or resins. Still others will be obvious to those of ordinary skill in the art having the benefit of this disclosure. For example, medical waste is sometimes disposed via incineration to avoid cross contamination with bacteria or pathogens. Accordingly, the elongated bag body 201 can be manufactured from a material that is combustible in one or more embodiments. Further, additives can be included in the material, such as odor-controlling additives, anti-microbial additives, and so forth.

In one embodiment, the elongated bag body 201 is manufactured from an extrusion process using high-density polyethylene. However, other manufacturing techniques can also be used. For example, the elongated bag body 201 can be manufactured by folding a high-density polyethylene or other plastic sheet. Further, the elongated bag body 201 can be manufactured by weaving polyethylene or impregnating another material with polyethylene.

In one embodiment, the elongated bag body 201 is color coded to indicate a particular use. For example, in one embodiment the elongated bag body 201 is opaque and is colored white so as to indicate it is to be used as a suture collection bag. The color could be used to indicate other characteristics as well, including the fact that the bag 200 is sterile and suitable for use in an operating room. In other embodiments, the elongated bag body 201 may have no color at all. For example, in one embodiment the elongated bag body 201 is clear.

In one or more embodiments, the material selected for the elongated bag body 201 is liquid-impervious and has a strong tinsel strength. Where high-density polyethylene is used to manufacture the elongated bag body 201, the resulting bag 200 is well suited for use in medical environments for the disposal of soft materials such as sutures, bandages, and gauze. High-density polyethylene is substantially impervious to water or other liquids and is capable of supporting relatively large amounts of weight. Accordingly, this allows the bag 200 to be used for the disposal of medical waste that is liquid-soaked by ensuring that the liquids remain within the interior of the bag 200.

It should be noted that the bag 200 can be made in any of a number of sizes and shapes. In one embodiment, the elongated bag body 201 has a length 205 of about twelve inches and a width 206 of about six inches. The term "about" is used to indicate a dimension inclusive of manufacturing tolerances. For example, if the manufacturing tolerances were plus or minus one-half inch, "about twelve inches" would include a range of 11.5 inches to 12.5 inches, and so forth. In one embodiment, the first major face 207 and second major face 307 of the elongated bag body 201 are twice as long as they are wide.

In the illustrative embodiment of FIGS. 2-5, the elongated bag body 201 is formed to define a first major face 207, shown as the front face of the bag 200 in FIG. 2, and a second major face 307, shown as the rear face of the bag 200 in FIG. 3. Two side portions 401,402 are disposed between the first major face 207 and the second major face 307.

Figure 4:
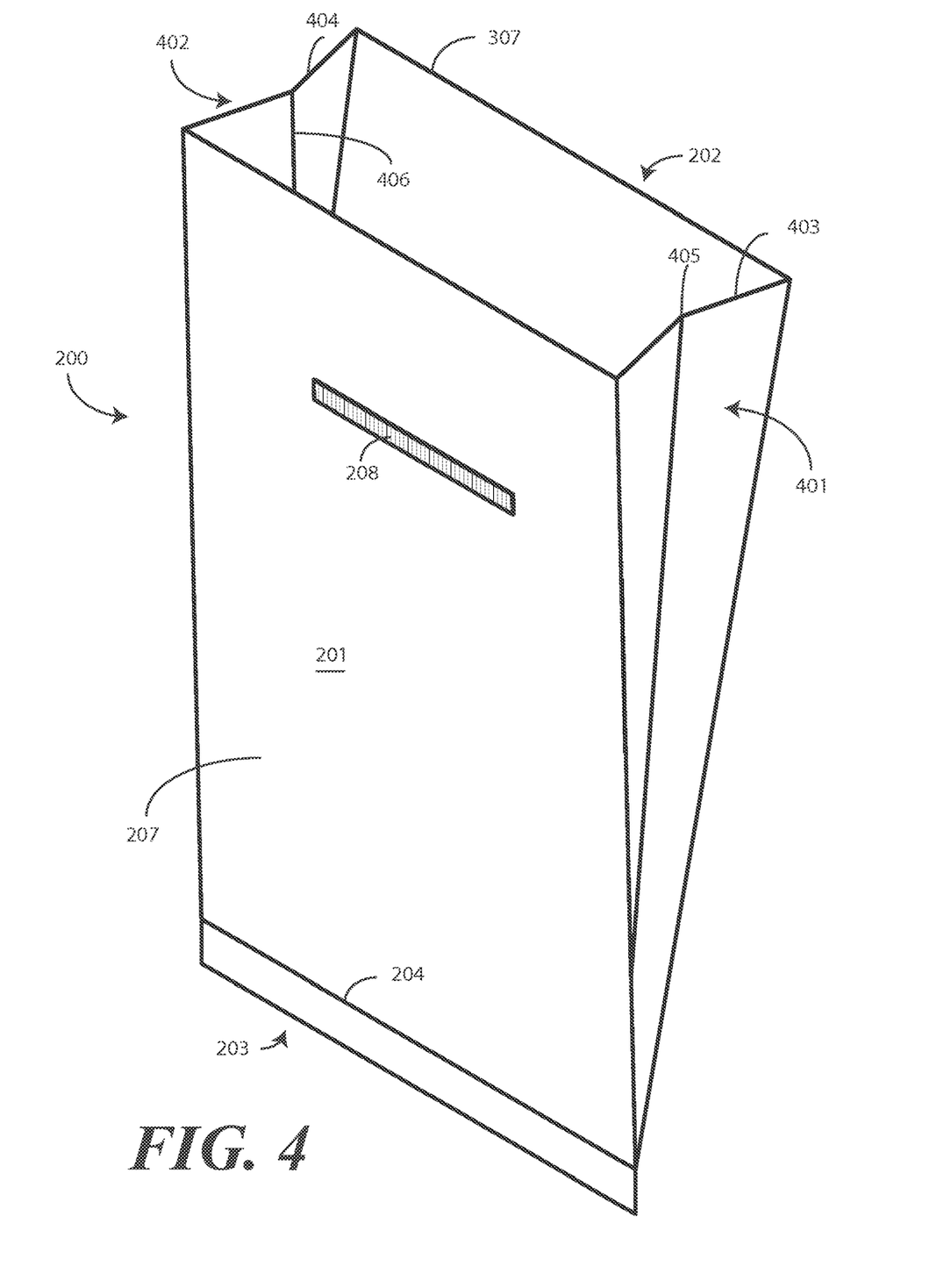
FIG. 4 illustrates a perspective view of one explanatory bag with an openable end in an open position in accordance with one or more embodiments of the disclosure.
Figure 5:
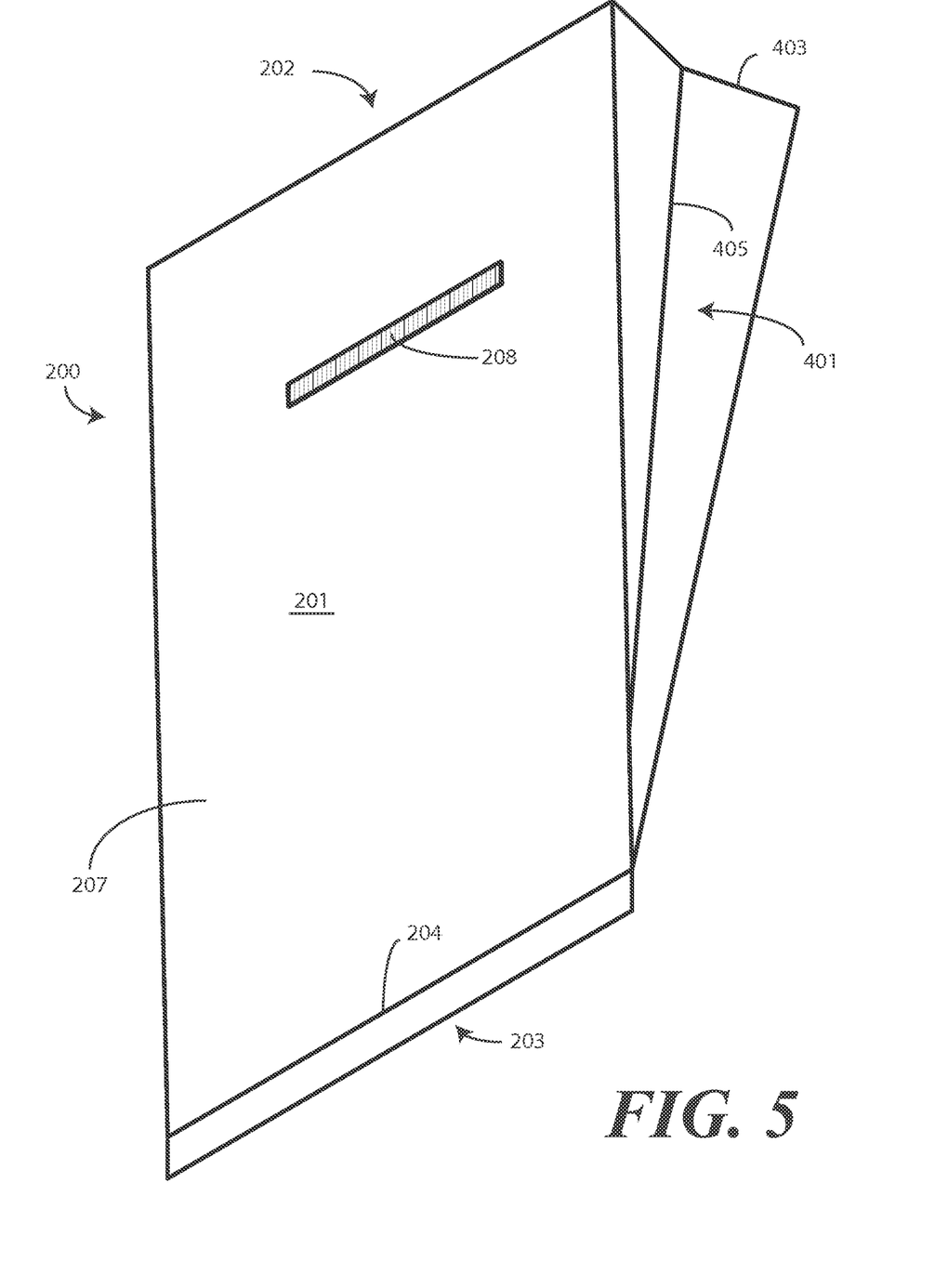
FIG. 5 illustrates another perspective view of one explanatory bag with an openable end in an open position in accordance with one or more embodiments of the disclosure.

In one embodiment, each side portion 401,402 comprises an accordion fold. For example, as best seen in FIG. 4, in one embodiment the elongated bag body 201 comprises a first accordion fold 403 and a second accordion fold 404. The first major face 207 and the second major face 307 are defined between the first accordion fold 403 and the second accordion fold 404. The illustrative accordion folds of FIG. 4 are inward facing, single accordion folds that have a folded midpoint 405,406. Each of the first accordion fold 403 and the second accordion fold 404 is expandable and expands when the openable end 202 is moved to the open position shown in FIGS. 4 and 5.

It should be noted that the first accordion fold 403 and the second accordion fold 404 can take different shapes. For example, while the first accordion fold 403 and the second accordion fold 404 in one embodiment is an inward facing, single accordion fold, more folds can be used. In one embodiment each of the first accordion fold 403 and the second accordion fold 404 can comprises two or more folds, with each fold having a width of one inch or less. Other fold configurations will be obvious to those of ordinary skill in the art having the benefit of this disclosure.

Figure 7:
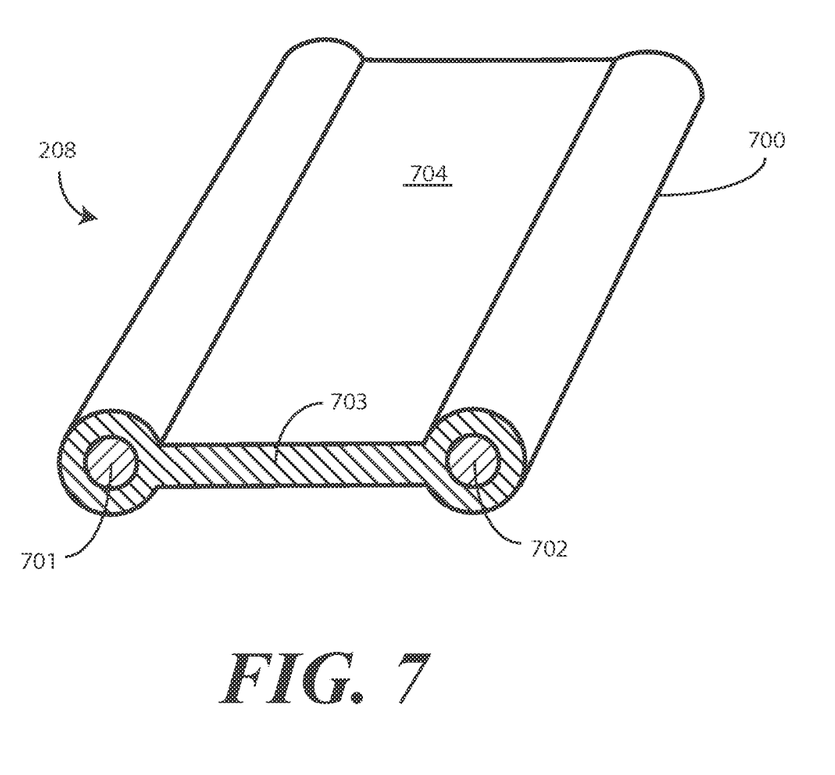
FIG. 7 illustrates one explanatory flexible strip in accordance with one or more embodiments of the disclosure.

In one embodiment, a flexible strip 208 is disposed upon an exterior of the elongated bag body 201. The flexible strip 208 can take a variety of forms. In one or more embodiments, the flexible strip 208 includes one or more wires or other bendable pieces of metal so as to be easily deformable to a desired shape. In one embodiment, the flexible strip 208 comprises a two-wire strip. While a two-wire strip will be used as an explanatory flexible strip 208 for illustrative purposes, it should be noted that the flexible strip 208 could include one wire, three wires, or more wires. Turning briefly to FIG. 7, illustrated therein is one example of such a two-wire strip 600.

As shown in FIG. 7, in one embodiment the flexible strip 208 is a two-wire strip 700 comprising two strands 701,702 of flexible wire disposed within a thermoplastic binder 703. In one embodiment, the flexible wire is a bendy wire manufactured from a malleable metal such as soft-annealed iron having a 26 or greater gauge measurement. Such wires are less than ten thousandths of an inch in diameter. Thicker wires can be used to stiffen the flexible strip 208. Moreover, in other embodiments the flexible strip 208 can be a single-wire strip, three-wire strip, four-wire strip, and so forth. In other embodiments, such as where the bag (200) will be subjected to radiation to kill microorganisms, bacteria, or pathogens, non-metallic malleable materials can be substituted for the wires described above. Still other configurations will be obvious to those of ordinary skill in the art having the benefit of this disclosure.

The thermoplastic binder 703 can be made from a variety of materials. In one or more embodiments, the thermoplastic binder 703 is manufactured from a flexible thermoplastic. Examples of flexible thermoplastics include polyvinyl materials, polystyrene, nylon, cellulose esters, and so forth. Polyethylene can also be used for the thermoplastic binder 703. In one or more embodiments the material selected for use as the thermoplastic binder 703 is one that securely bonds to the strands 701,702.

In one or more embodiments, the center 704 of the two-wire strip 700 can be textured.

For example, it can include one or more bumps, protrusions, slits, or other surface features that assist a user in grasping the two-wire strip 700 during a bending operation. Further, the thermoplastic binder 703 can be color-coded to indicate, for example, that the bag (200) is specifically designed as a suture bag, a medical waste bag, or other type of bag.

In one or more embodiments, the two-wire strip 700 is manufactured via an extrusion process. In one explanatory extrusion process, the strands 701,702 are passed through an extruder that applies the thermoplastic binder 703 about the strands 701,702.

Turning now back to FIGS. 2-5, in one embodiment the flexible strip 208 is adhesively disposed along the exterior of the elongated bag body 201. In this illustrative embodiment, the flexible strip 208 is disposed on the front major face of the elongated bag body 201 as shown in FIG. 2.

In one embodiment, and adhesive strip 308 is also disposed along the exterior of the elongated bag body 201. In this illustrative embodiment, the adhesive strip 308 is disposed horizontally along the rear major face of the elongated bag body 201 as shown in FIG. 3. In one embodiment the adhesive strip 308 is initially covered with a releasable liner 309 that is disposed atop the adhesive strip 308. A user can remove the releasable liner 309 to reveal the adhesive strip 308 so that the bag 200 can be attached to a surface such as an operating table, wall, cabinet, cart, or other object.

In one embodiment, indicia 312 are disposed on the exterior of the elongated bag body 201 instructing removal of the releasable liner 309. In this illustrative embodiment the indicia 312 include the words "remove liner" and two arrows. Other indicia can be included on the bag 200 as well. As shown in FIG. 2, the first major face 207 can include brand information, manufacturer information, and other information. In one embodiment, the first major face 207 includes indicia 212 disposed on the exterior of the elongated bag body 201 indicating the bag is to receive sutures.

In the illustrative embodiment of FIGS. 2-5, the flexible strip 208 and the adhesive strip 308 are disposed on opposite major faces of the elongated bag body 201. In this embodiment, the flexible strip 208 is disposed on the first major face 207, while the adhesive strip 308 is disposed on the second major face 307. However, the opposite could be true, with the flexible strip 208 disposed on the second major face 307, while the adhesive strip 308 is disposed on the first major face 207. Further, both the flexible strip 208 and the adhesive strip 308 may be disposed on a single major face, be it the first major face 207 or the second major face 307. Other configurations will be obvious to those of ordinary skill in the art having the benefit of this disclosure.

In one or more embodiments, the flexible strip 208 and the adhesive strip 308 are disposed nearer to the openable end 202 than the closed end 203. This is best shown in FIGS. 2 and 3. In one embodiment, the elongated bag body 201 defines a length 205 and the flexible strip 208 and the adhesive strip 308 are disposed a distance of ten percent or less of the length 205 from the openable end 202. In the illustrative embodiment of FIGS. 2-5, the top 210 of the flexible strip 208 and the top 310 of the adhesive strip 308 are one centimeter or less from the openable end 202, which is less than ten percent of the length 205 when the length 205 is about twelve centimeters.

In one embodiment, a width 211 of the flexible strip 208 and a width 311 of the adhesive strip 308 are each less than a width 206 of the major faces of the elongated bag body 201. In one embodiment, the width 311 of the adhesive strip 308 is greater than the width 211 of the flexible strip 208. Other configurations will be obvious to those of ordinary skill in the art having the benefit of this disclosure.

Figure 6:
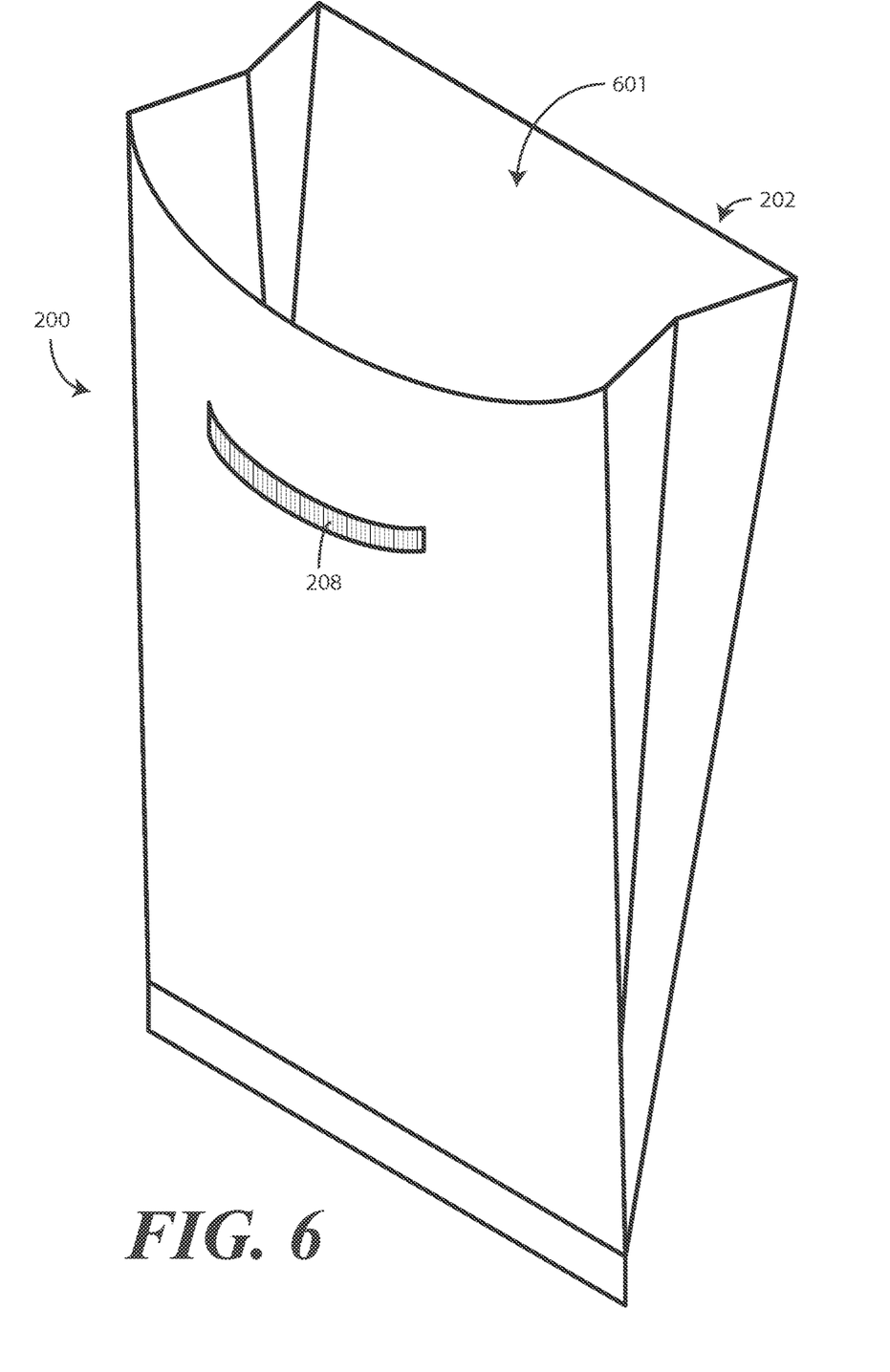
FIG. 6 illustrates a perspective view of one explanatory bag with a bendable flexible strip bent to retain an openable end in the open position in accordance with one or more embodiments of the disclosure.

In one or more embodiments, the flexible strip 208 is bendable to retain the openable end 202 in an open position. This is shown in FIG. 6. Turning now to FIG. 6, a user has bent the bendable and/or flexible strip 208 to retain the openable end 202 of the bag 200 in the open position 601. The inclusion of the bendable and/or flexible strip 208 is advantageous because the bendable and/or flexible strip 208 can retain the openable end 202 of the bag 200 in the open position 601 regardless of whether the bag 200 is positioned horizontally or vertically. Accordingly, a user can attach the adhesive strip (308) to a vertical surface, such as a cabinet, or a horizontal surface, such as a surgical cart or operating table, and still retain the openable end 202 in the open position 601.

When the bag 200 is in the open position 601, the flexible strip 208 is malleable so as to be adjustable into different shapes. Accordingly, a user can bend the flexible strip 208 such that the openable end 202 takes any of a variety of shapes, including semi-circular, angular, elliptical, or free form shapes.

Figure 8:
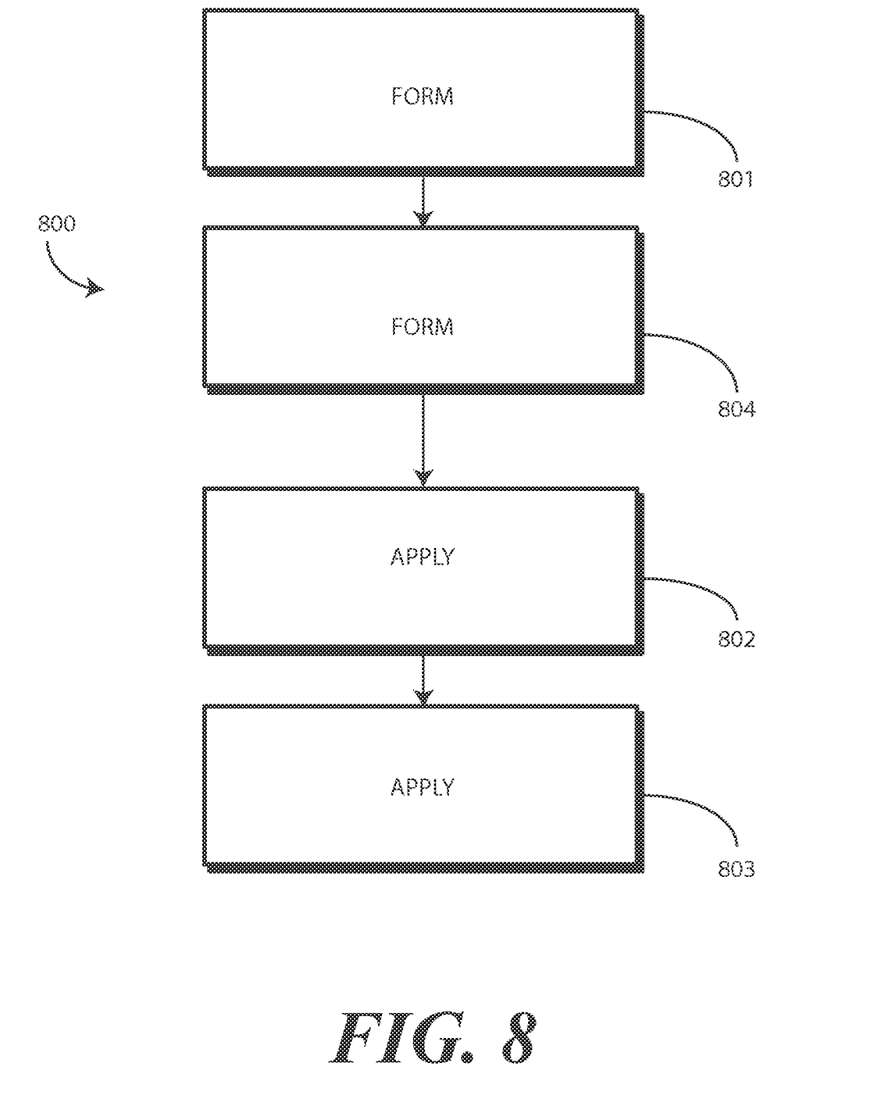
FIG. 8 illustrates one explanatory method of manufacturing a bag in accordance with one or more embodiments of the disclosure.
Figure 9:
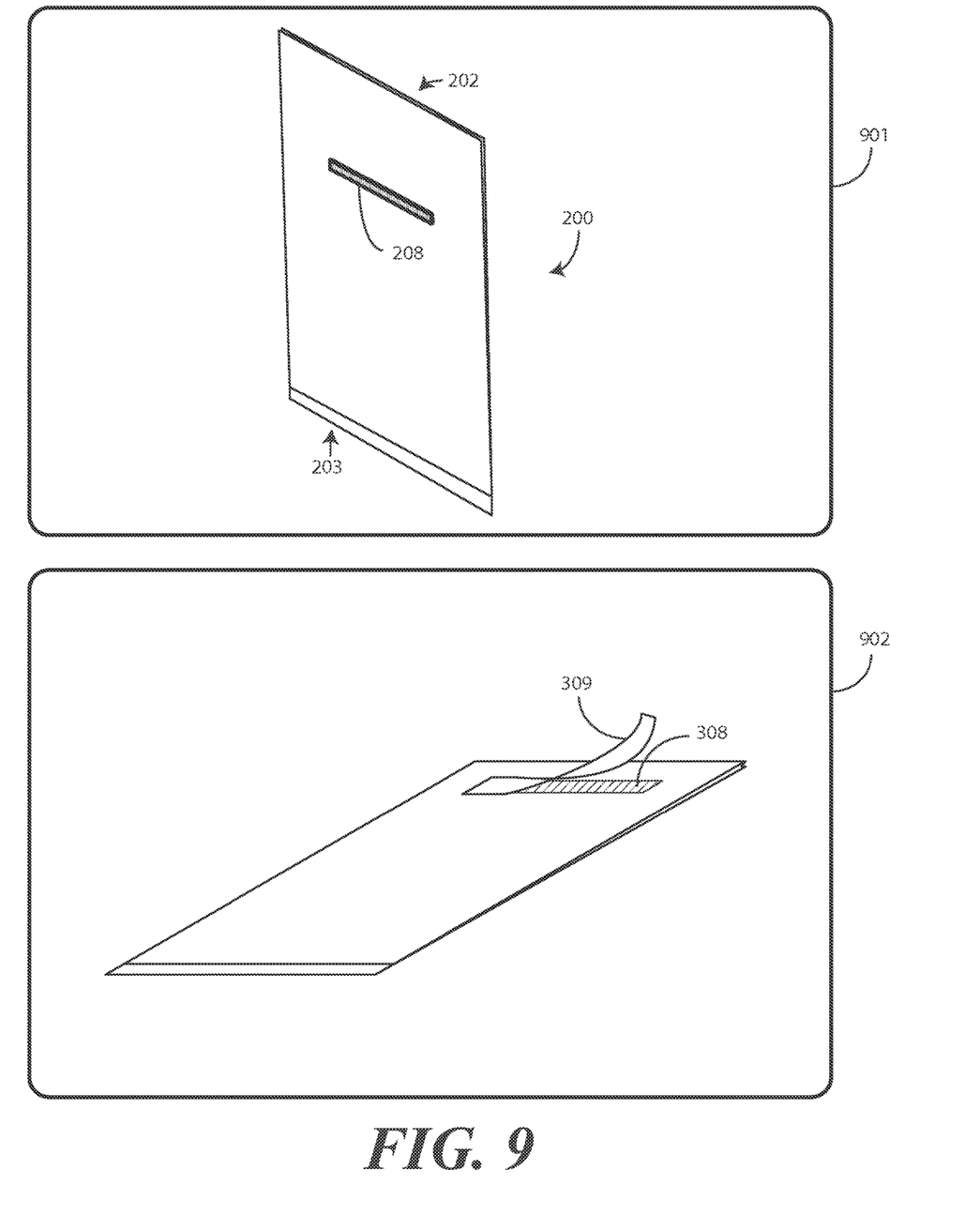
FIG. 9 illustrates explanatory steps of a method of using a bag in accordance with one or more embodiments of the disclosure.

Turning now to FIG. 8, illustrated therein is a method 800 for manufacturing a bag in accordance with one or more embodiments of the disclosure. At step 801, the method 800 forms a bag body defining an openable end and a closed end. In one embodiment, this step 801 is performed by extruding an elongated bag body and thermally sealing one end to form a bag. In one embodiment, the openable end and the closed end are disposed at distally opposite end of the bag body. For example, the openable end can be disposed at a first end of the bag body while the closed end is disposed distally along the bag body from the open end at a second end of the bag body. Optional step 804 can be included in which side portions are formed by forming a first accordion fold and a second accordion fold along the bag body.

At step 802, the method 800 applies a flexible strip to an exterior of the bag body. In one embodiment, this step 802 comprises adhesively applying the flexible strip to the exterior of the bag body. Other techniques, such as thermally attaching the flexible strip to the exterior of the body may also be used at step 802. In one embodiment, the flexible strip is bendable to retain the openable end formed at step 801 in the open position.

At step 803, the method 800 additionally applies an adhesive strip to the exterior of the bag body. In one or more embodiments, the applying of step 802 and the additional applying of step 803 comprise disposing the flexible strip and the adhesive strip on opposite sides of the bag body and closer to the openable end than the closed end. Where optional step 804 is included, the applying of step 802 and the additional applying of step 803 can comprise placing both the flexible strip and the adhesive strip between the accordion folds such that the first accordion fold and second accordion fold are disposed between the flexible strip and the adhesive strip.

Turning now to FIGS. 9-12, illustrated therein are explanatory steps for using a bag in accordance with one or more embodiments of the disclosure. Beginning with FIG. 9, at step 901 a user obtains a bag 200. In one embodiment, the bag 200 defines an openable end 202 and a closed end 203. In one embodiment, the bag 200 also includes a flexible strip 208 and an adhesive strip 308 (shown in step 902), each being disposed on an exterior of the bag 200. At step 902, a user removes the releasable liner 309 disposed atop the adhesive strip 308 to reveal the adhesive strip 308.

Figure 10:
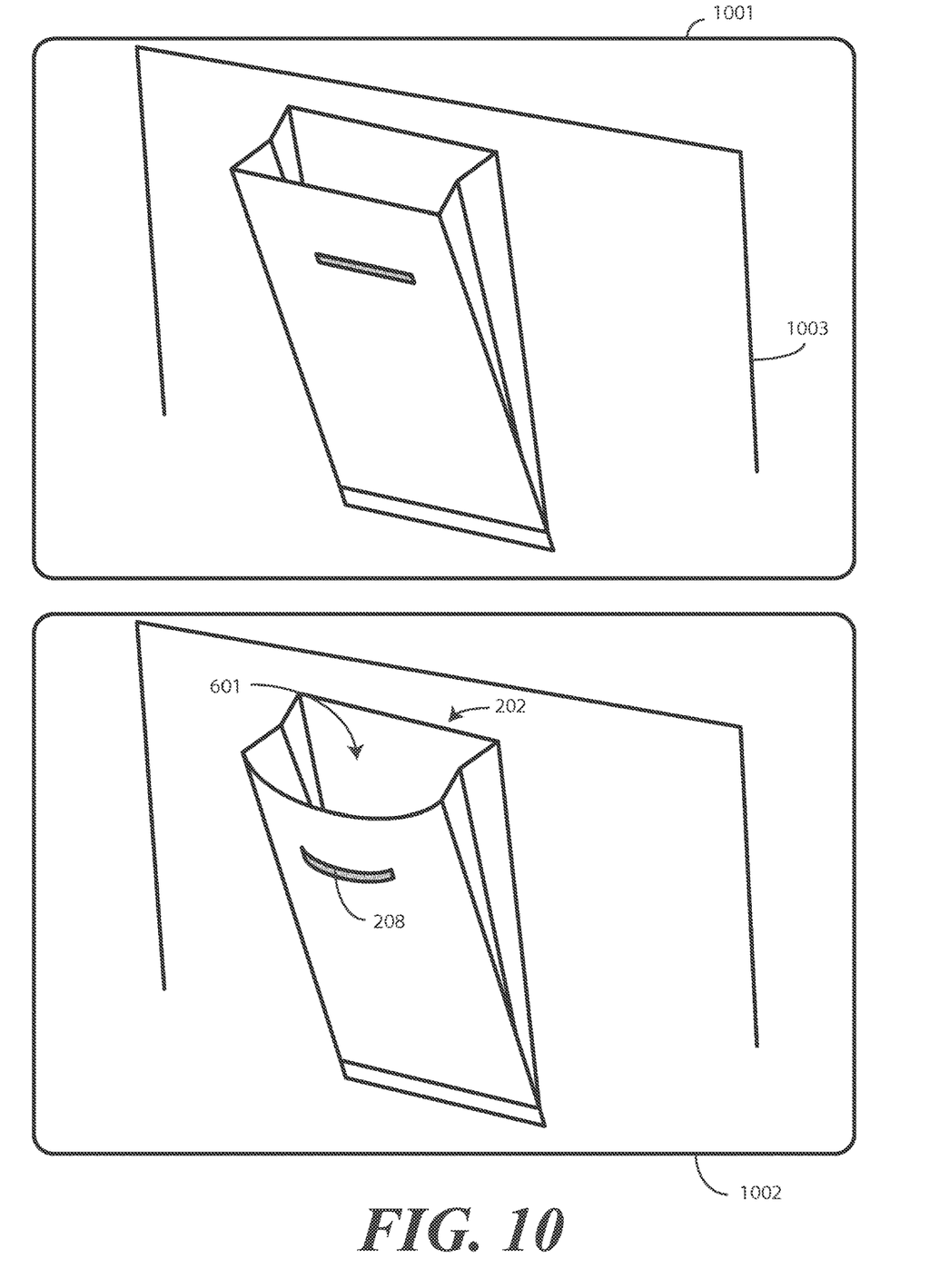
FIG. 10 illustrates explanatory steps of a method of using a bag in accordance with one or more embodiments of the disclosure.

Turning to FIG. 10, at step 1001 a user has attached the adhesive strip (308) to a surface 1003. In this illustrative embodiment, the surface 1003 is a vertical surface. However, as previously described the surface 1003 could also be a horizontal surface. At step 1002, a user has bent the flexible strip 208 to retain the openable end 202 in an openable position.

Figure 11:
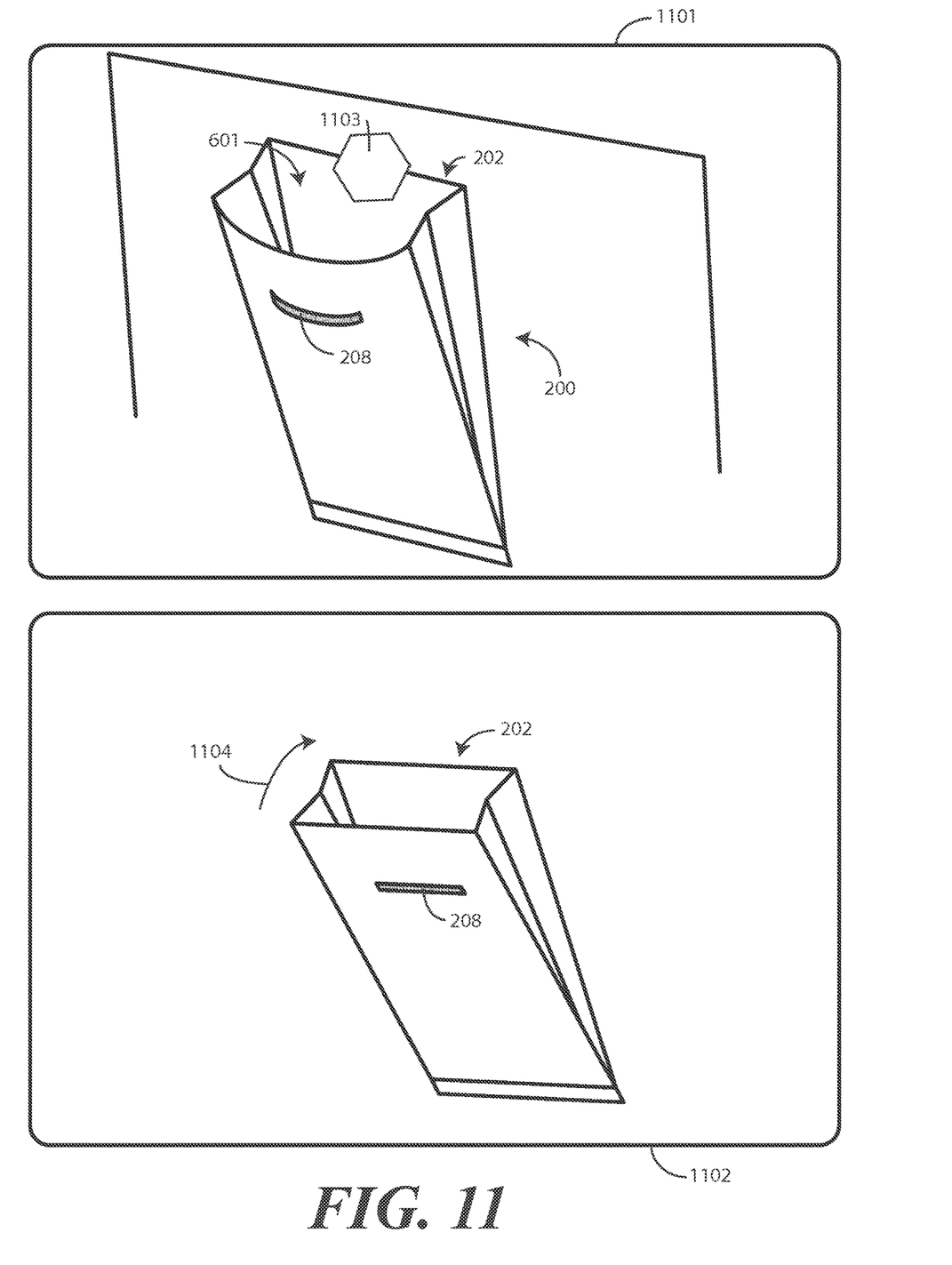
FIG. 11 illustrates explanatory steps of a method of using a bag in accordance with one or more embodiments of the disclosure.

Turning to FIG. 11, at step 1101 a user then deposits medical waste 1103 into the openable end 202 of the bag 200. Said differently, in one embodiment at step 1101 the user inserts the medical waste 1103 into the bag 200 through the openable end 202. In one embodiment, the medical waste 1103 is suture material. The user need not worry about the openable end 202 closing due to the fact that the flexible strip 208 retains the openable end 202 in the open position 601.

Figure 12:
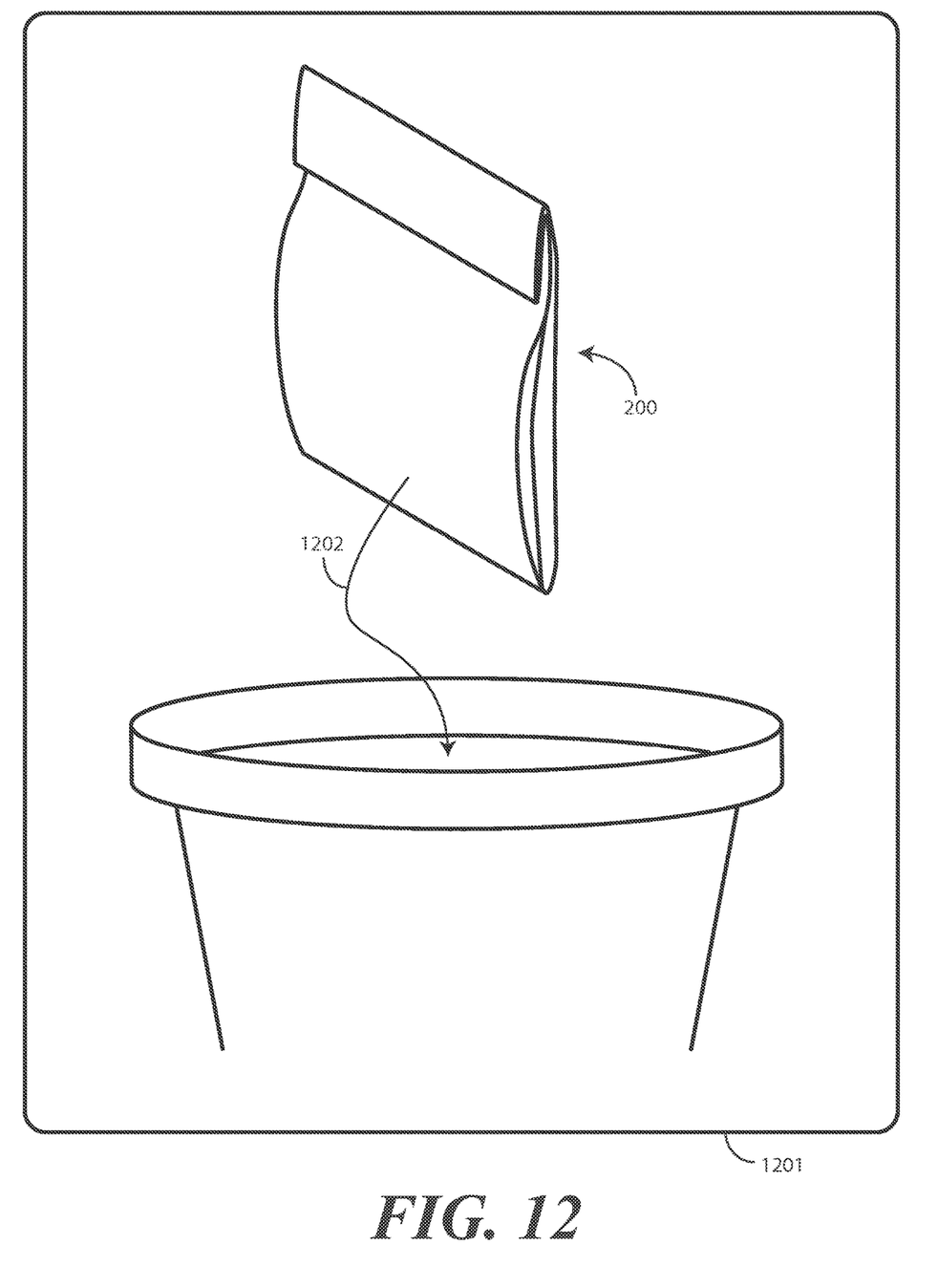
FIG. 12 illustrates one explanatory step of a method of using a bag in accordance with one or more embodiments of the disclosure.

At step 1102 the user then rebends the flexible strip 208 to return 1104 the openable end 202 to the closed position, which is shown in FIG. 12 at step 1201. The user can then dispose 1202 of the bag 200 in accordance with standard disposal procedures.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A bag, comprising:
    an elongated bag body defining a first major face, a second major face, and two opposing ends, the two opposing ends comprising an openable end and a closed end;
    an adhesive strip applied to an exterior of the second major face of the elongated bag body and attachable to a surface; and
    a flexible strip adhesively applied to the exterior of the first major face of the elongated bag body;
    the flexible strip bendable to retain the openable end in an open position;
    a width of the flexible strip less than another width of a major face of the elongated bag body;
    the elongated bag body defining a flattened shape when the openable end is in a closed position;
    the elongated bag body comprising a first side portion between the first major face and the second major face and a second side portion between the first major face and the second major face, the first side portion and the second side portion defining a triangular shape when the openable end is in the open position;
    the first side portion comprising a first accordion fold and the second side portion comprising a second accordion fold, the first accordion fold and the second accordion fold each comprising inward facing, single accordion folds having a folded midpoint; and
    the elongated bag body defining a length, the flexible strip applied only to the first major face at a distance of ten percent or less of the length from the openable end.

2. The bag of claim 1, a width of the the adhesive strip less than the another width of the major face, the width of the flexible strip less than the width of the adhesive strip.

3. The bag of claim 1, the flexible strip comprising a two-wire flexible strip with a textured center.

4. The bag of claim 3, the elongated bag body manufactured from an extrusion process using high-density polyethylene.

5. The bag of claim 4, the elongated bag body opaque.

6. The bag of claim 5, the elongated bag body white.

7. The bag of claim 1, further comprising a releasable liner disposed atop the adhesive strip.

8. The bag of claim 7, further comprising indicia disposed on the exterior of the elongated bag body instructing removal of the releasable liner.

9. The bag of claim 1, the elongated bag body twice as long as wide.

10. The bag of claim 1, the closed end thermally closed by a thermal seal sealing the first major face to the second major face at the closed end.

11. The bag of claim 1, further comprising indicia disposed on the exterior of the elongated bag body indicating the bag is to receive sutures.

12. A method of manufacturing a bag, comprising:
forming a bag body defining an openable end and a closed end disposed distally along the bag body from the openable end;
thermally applying a flexible strip having a width less than the bag body only to an exterior of a first major face of the bag body; and
additionally applying an adhesive strip only to an exterior of a second major face of the bag body;
the flexible strip bendable to retain the openable end in an open position.

13. The method of claim 12, the thermally applying and the additionally applying comprising applying the flexible strip and the adhesive strip with a width of the adhesive strip being less than a width of the second major face, and with a width of the flexible strip being less than the width of the adhesive strip.

14. The method of claim 13, further comprising forming a first accordion fold and a second accordion fold between the flexible strip and the adhesive strip, the first accordion fold and the second accordion fold defining a flattened shape when the openable end is in a closed position, and a triangular shape when the openable end is in the open position.

15. The method of claim 14, further comprising thermally sealing the first major face and the second major face together at the closed end.

16. A bag, comprising:
an elongated bag body defining a first major face, a second major face, and two opposing ends, the two opposing ends comprising an openable end and a closed end;
an adhesive strip applied to an exterior of the second major face of the elongated bag body and attachable to a surface; and
a flexible strip adhesively applied to the exterior of the first major face of the elongated bag body;
the flexible strip bendable to retain the openable end in an open position;
a width of the flexible strip less than another width of a major face of the elongated bag body;
the elongated bag body defining a flattened shape when the openable end is in a closed position;
the elongated bag body comprising a first side portion between the first major face and the second major face and a second side portion between the first major face and the second major face, the first side portion and the second side portion defining a triangular shape when the openable end is in the open position;
the first side portion comprising a first accordion fold and the second side portion comprising a second accordion fold, the first accordion fold and the second accordion fold each comprising inward facing, single accordion folds having a folded midpoint; and
the flexible strip comprising a two-wire flexible strip with a textured center.

17. The bag of claim 16, the elongated bag body manufactured from an extrusion process using high-density polyethylene.

18. The bag of claim 17, the elongated bag body opaque.

19. The bag of claim 18, the elongated bag body white.

20. The bag of claim 16, further comprising a releasable liner disposed atop the adhesive strip.

* * * * *